US010617827B2

(12) United States Patent
Hautaviita et al.

(10) Patent No.: US 10,617,827 B2
(45) Date of Patent: Apr. 14, 2020

(54) MEDICAMENT DELIVERY DEVICE WITH USER FEEDBACK CAPABILITY

(71) Applicant: Carebay Europe Ltd., Sliema (MT)

(72) Inventors: Nikolaj Hautaviita, Bro (SE); Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 0 days.

(21) Appl. No.: 16/065,804

(22) PCT Filed: Nov. 23, 2016

(86) PCT No.: PCT/EP2016/078501
§ 371 (c)(1),
(2) Date: Jun. 23, 2018

(87) PCT Pub. No.: WO2017/108312
PCT Pub. Date: Jun. 29, 2017

(65) Prior Publication Data
US 2019/0009032 A1 Jan. 10, 2019

(30) Foreign Application Priority Data
Dec. 23, 2015 (EP) ..................................... 15202498

(51) Int. Cl.
*A61M 5/31* (2006.01)
*A61M 5/315* (2006.01)
*A61M 5/24* (2006.01)

(52) U.S. Cl.
CPC ...... *A61M 5/3157* (2013.01); *A61M 5/31551* (2013.01); *A61M 5/31585* (2013.01);
(Continued)

(58) Field of Classification Search
CPC ...... A61M 5/1723; A61M 2005/14296; A61M 2230/201; A61M 5/14; A61M 5/16804;
(Continued)

(56) References Cited

U.S. PATENT DOCUMENTS 5,593,390 A * 1/1997 Castellano ........ A61M 5/31553
604/187
2011/0313395 A1* 12/2011 Krulevitch .............. A61M 5/24
604/504
(Continued)

FOREIGN PATENT DOCUMENTS

EP 1804868 B1 12/2009
WO 2013004844 A1 1/2013
(Continued)

Primary Examiner — Michael P Stafira
(74) Attorney, Agent, or Firm — McDonnell Boehnen Hulbert & Berghoff LLP

(57) ABSTRACT

The present disclosure relates to a medicament delivery device comprising: a housing (3), a plunger rod received by the housing (3), which plunger rod is rotatable in a first direction relative to the housing (3) and linearly displaceable, an activation button arrangement linearly displaceable from a first position to a second position to thereby rotate the plunger rod in the first direction, a second direction rotation preventer having an annular outer member that is rotationally fixed relative to the housing (3) and an annular inner member partially received by the outer member, wherein the outer member and the inner member are arranged to receive the plunger rod and wherein the inner member is rotationally interlocked with the plunger rod, wherein the outer member and the inner member are structured to allow the inner member to rotate in the first direction relative to the outer member and to prevent the inner member from rotating in a second direction opposite to the first direction, and a recording unit (5) comprising: a first sensor arranged to detect rotation of the inner member, and processing circuitry configured to generate dose expulsion data in response to detection of rotation of the inner member.

4 Claims, 8 Drawing Sheets

(52) U.S. Cl.
CPC . *A61M 5/31593* (2013.01); *A61M 2005/2407* (2013.01); *A61M 2005/3126* (2013.01); *A61M 2205/3306* (2013.01); *A61M 2205/3317* (2013.01); *A61M 2205/3561* (2013.01); *A61M 2205/50* (2013.01); *A61M 2205/502* (2013.01); *A61M 2205/581* (2013.01); *A61M 2205/582* (2013.01)

(58) Field of Classification Search
CPC ............ A61M 2205/52; A61M 25/007; A61M 5/14248; A61M 5/1456; A61M 5/31553; A61M 5/31583; A61M 2005/3126; A61M 2205/50; A61M 2205/583; A61M 31/007; A61M 5/20; A61M 5/24; A61M 5/31541; A61M 5/31593; A61M 15/008; A61M 15/0081; A61M 15/0083; A61M 2005/31518; A61M 2205/3561; A61M 2005/14252; A61M 2005/14268; A61M 2005/1583; A61M 2005/1585; A61M 2005/3142; A61M 2205/3592; A61M 2205/6054; A61M 2209/045; A61M 5/1413; A61M 5/14244; A61M 5/158; A61M 5/31568; A61M 2205/3306; A61M 2205/3584; A61M 2205/8212; A61M 37/00; A61M 5/28; A61M 5/3146; A61M 2005/14264; A61M 2005/2474; A61M 2205/33; A61M 2205/3331; A61M 2205/581; A61M 5/16831; A61M 5/2033; A61M 5/31531; A61M 5/3157; A61M 5/32; A61M 5/42; A61M 11/06; A61M 15/00; A61M 15/0045; A61M 15/08; A61M 2205/0266; A61M 2205/073; A61M 2205/15; A61M 2205/276; A61M 2205/609; A61M 2207/00; A61M 2209/086; A61M 2210/0618; A61M 5/142; A61M 5/14566; A61M 5/1684; A61M 5/16854; A61M 5/172; A61M 5/3129; A61M 5/31525; A61M 5/31551; A61M 5/31556; A61M 5/3158; A61M 2205/215; A61M 2205/3317; A61M 2205/3553; A61M 5/2455; A61M 5/31536; A61M 5/31571; A61M 5/31585; A61M 2005/2407; A61M 2205/14; A61M 2205/18; A61M 2205/332; A61M 2205/3569; A61M 2205/582; A61M 2205/584; A61M 2205/585; A61M 2205/6081; A61M 2209/04; A61M 5/31; A61M 5/315; A61M 5/31501; A61M 5/31528; A61M 5/3156; A61M 5/31566; A61M 2005/2073; A61M 2005/2433; A61M 2005/3125; A61M 2005/31508; A61M 2005/3152; A61M 2005/3154; A61M 2205/3313; A61M 2205/3327; A61M 2205/6063; A61M 2205/6072; A61M 2205/70; A61M 2205/8293; A61M 5/14216; A61M 5/1452; A61M 5/1454; A61M 5/1782; A61M 5/30; A61M 5/31511; A61M 5/31515; A61M 5/31535; A61M 5/3155; A61M 5/31561; A61M 5/31563; A61M 5/31573; A61M 5/31596; A61M 5/482; G02B 27/106; G02B 27/141; G02B 5/208; G02B 27/022

See application file for complete search history.

(56) References Cited

U.S. PATENT DOCUMENTS

2016/0114109 A1* 4/2016 Lavi .................... A61M 5/1452
604/82
2016/0263327 A1* 9/2016 Radmer .................. A61M 5/20

FOREIGN PATENT DOCUMENTS

WO     2013058698 A1    4/2013
WO     2014037331 A1    3/2014

* cited by examiner

MEDICAMENT DELIVERY DEVICE WITH USER FEEDBACK CAPABILITY

CROSS REFERENCE TO RELATED APPLICATIONS

The present application is a U.S. National Phase Application pursuant to 35 U.S.C. § 371 of International Application No. PCT/EP2016/078501 filed Nov. 23, 2016, which claims priority to European Patent Application No. 15202498.0 filed Dec. 23, 2015. The entire disclosure contents of these applications are hereby incorporated by reference into the present application.

TECHNICAL FIELD

The present disclosure generally relates to medical devices. In particular, it relates to a medicament delivery device.

BACKGROUND

When administering a medicament by means of a medicament delivery device, it may for certain applications be of importance to register the time of administration and the size of the dose.

Traditionally, such logs were kept manually by the user. This however required that the user was able to remember to write down the correct information at every occasion of medicament administration. The disadvantages of this method have resulted in a drive towards the development of medicament delivery devices that can handle logging automatically.

An example of such automatic logging is disclosed in EP1804868. This document discloses a medication delivery device that comprises an injection device having a reservoir comprising a medicament to be ejected, and a sensor arranged to detect an ejection of the medicament from the injection device, and a processor. The sensor is arranged to output a signal comprising ejecting information. The processor collects and stores the ejection information.

The medicament delivery device disclosed in EP1804868 is of the type which has a piston rod that is displaced linearly inside the housing without rotation relative to the housing.

There are however medicament delivery devices on the market that have piston rods provided with a threaded outer surface, where linear displacement of the plunger rod is achieved by means of rotation thereof. For these types of medicament delivery devices there are currently no solutions for automatic logging where it can be made certain that detection of displacement of internal parts can be attributed to medicament administration.

SUMMARY

In view of the above, a general object of the present disclosure is to provide a medicament delivery device that solves or at least mitigates the problems of the prior art.

There is hence provided a medicament delivery device comprising: a housing, a plunger rod received by the housing, which plunger rod is rotatable in a first direction relative to the housing and linearly displaceable thereby, an activation button arrangement linearly displaceable from a first position to a second position to thereby rotate the plunger rod in the first direction, a second direction rotation preventer having an annular outer member that is rotationally fixed relative to the housing and an annular inner member partially received by the outer member, wherein the outer member and the inner member are arranged to receive the plunger rod and wherein the inner member is rotationally interlocked with the plunger rod, wherein the outer member and the inner member are structured to allow the inner member to rotate in the first direction relative to the outer member and to prevent the inner member from rotating in a second direction opposite to the first direction, and a recording unit comprising: a first sensor arranged to detect rotation of the inner member, and processing circuitry configured to generate dose expulsion data in response to detection of rotation of the inner member. It may also be conceivable that the first sensor is arranged to detect rotation of the inner member and/or any of its components thereof.

By detecting rotation of the inner member and/or any of its components thereof it can be made certain that the first sensor only detects motion during drug administration, i.e. when the plunger rod is rotated in the first direction and thereby linearly displaced. This is because the inner member is rotatable only in the first direction by the plunger rod, as the plunger rod is rotated and thereby displaced linearly.

According to one embodiment one of the inner member and the outer member has a ratchet along the circumference thereof and the other one of the inner member and the outer member has a flexible radial arm arranged to interact with the ratchet, to allow rotation of the inner member in the first direction and to prevent rotation of the inner member in the second direction.

According to one embodiment the inner member has as an outer periphery provided with a plurality of recesses, wherein the first sensor is an electromechanical switch in physical contact with the outer periphery of the inner member, and wherein the electromechanical switch is arranged to be actuated by interaction with the recesses.

According to one embodiment the processing circuitry is configured to determine the number of times the electromechanical switch is moved in and out from the recesses during one drug administration, and wherein the processing circuitry is configured to determine an injected dose based on the determined number of times the electromechanical switch is moved in and out from the recesses.

According to one embodiment the inner member has an outer periphery provided with a plurality of through-openings, wherein the first sensor is a photo interrupter having an electromagnetic wave emitter and an electromagnetic wave sensor, and wherein the openings are arranged to extend in between the electromagnetic wave emitter and electromagnetic wave sensor.

One embodiment comprises an image acquisition unit and an electromagnetic wave emitter, wherein the inner member has an outer periphery provided with a visual pattern and wherein the electromagnetic wave emitter is configured to emit electromagnetic waves onto the visual pattern, wherein the first sensor is an optical sensor arranged to capture electromagnetic waves reflected by the visual pattern, wherein the image acquisition unit is configured to generate images of captured reflected electromagnetic waves, and wherein the processing circuitry is configured to determine whether the inner member is being rotated based on the images.

According to one embodiment the inner member has an outer periphery provided with a plurality of first cogs, wherein the recording unit includes a cog wheel provided with a plurality of second cogs arranged to engage with the first cogs, and wherein the first sensor is configured to detect rotation of the inner member by detecting rotation of the cog wheel.

According to one embodiment the first sensor is a photo interrupter having an electromagnetic wave emitter and an electromagnetic wave sensor, and wherein the second cogs are arranged to extend in between the electromagnetic wave emitter and electromagnetic wave sensor.

According to one embodiment the first sensor is a rotary position sensor arranged to detect rotation of the inner member by detecting rotation of the cog wheel.

According to one embodiment the cog wheel includes a magnet, and wherein the first sensor is a contactless magnetic sensor arranged to detect rotation of the inner member by detecting rotation of the cog wheel.

According to one embodiment the outer member has a first electric terminal and a second electric terminal, and the teeth of the ratchet are electrically conductive, wherein a first set of teeth are electrically connected to the first electric terminal and a second set of teeth are electrically connected to the second electric terminal, wherein the inner member has two flexible radial arms arranged to interact with the ratchet, which two flexible radial arms are electrically conductive and in electrical connection with each other, and wherein the recording unit has a power supply connectable to the first electric terminal and to the second electric terminal, wherein the first sensor is configured to detect rotation of the inner member by detecting closed circuits between the first electric terminal and the second electric terminal.

According to one embodiment the housing has an opening exposing the inner member, and wherein the recording unit is an add-on device attachable to the housing.

According to one embodiment the recording unit comprises a second sensor arranged to detect attachment of the recording unit to the housing. Further, the second sensor is arranged to activate the electronic components of the recording unit, such as the first sensor, the processing circuitry, and the transmitter.

According to one embodiment the recording unit is integrated with the housing.

One embodiment comprises a display unit configured to display the dose expulsion data. The display unit is preferably an electrophoretic (E-ink) display. Further, the dose expulsion data comprises information about the date and time when the last dose of medicament was administered. It also comprises information of whether synchronisation for data transfer to an external device has been successful or not. The dose expulsion data may according to one variation also comprises information about the size of the latest dose taken.

According to a further embodiment, the recording unit comprises a transmitter arranged to wirelessly transmit the dose expulsion data generated by a processing circuitry, to an external device such as a smart device, e.g. a smart phone or a tablet computer, or to a personal computer. The transmitter includes an antenna, which may be arranged to transmit the dose expulsion data over Bluetooth®, Wi-Fi™ or a cellular radio access network (RAN) such as Wideband Code Division Multiple Access (WCDMA) Long Term Evolution (LTE) and the 5G standard.

According to another aspect of the invention, the recording unit comprises a unique identifier which is transmitted with the dose expulsion data when a dose of medicament has been administered for facilitating compliance/adherence.

It is also a further object of the present invention that the medicament delivery device may be a regular medicament delivery device for medicament administration such as a manual injector and may be preferably a multi-use medicament delivery device or a trainer device.

According to a further embodiment, the first sensor is a combination of first sensors according to the preceding embodiments and wherein the processing circuitry is configured to receive, process and generate a compensated and accurate dose expulsion data in response to detection of rotation of the inner member.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which:

FIG. 12b shows a perspective view of a variation of the fourth example in FIG. 12a;

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein refers to that end of the medicament delivery device at which medical expulsion can be provided. This is hence that end of the medicament delivery device that is to be pointed towards the injection or expulsion site. This definition also extends to any internal or external component of the medicament delivery device, i.e. the proximal end of any component is that which is closest to the proximal end of the medicament delivery device. The "distal end" is the opposite end relative to the proximal end. With "proximal direction" is meant a direction from the distal end towards the proximal end, along the central axis of the medicament delivery device. With "distal direction" is meant the opposite direction to "proximal direction".

This disclosure relates to a medicament delivery device having a housing, and which is of the type that has a rotatable and thereby linearly displaceable plunger rod, manoeuvrable linearly in the proximal direction by an activation button arrangement, whereby medicament is expelled from the medicament delivery device. The plunger rod is only rotatable in one direction, a first direction. This rotation displaces the plunger rod in the proximal direction.

The medicament delivery device has a second direction rotation preventer including an annular inner member and an annular outer member arranged to receive the plunger rod. The inner member is partially received by the outer member. The outer member is rotationally fixed relative to the housing, and the inner member is rotationally interlocked with the plunger rod so that the inner member and the plunger rod can rotate in the first direction concurrently. The outer member and the inner member are structured such that the inner member is allowed to rotate in the first direction relative to the outer member and to prevent the inner member from rotating in a second direction opposite to the first direction.

The medicament delivery device may for example be an injector e.g. a manual injector, and is preferably a multi-use medicament delivery device. The medicament delivery device may be a regular medicament delivery device for medicament administration, or a trainer device.

Figure 1:
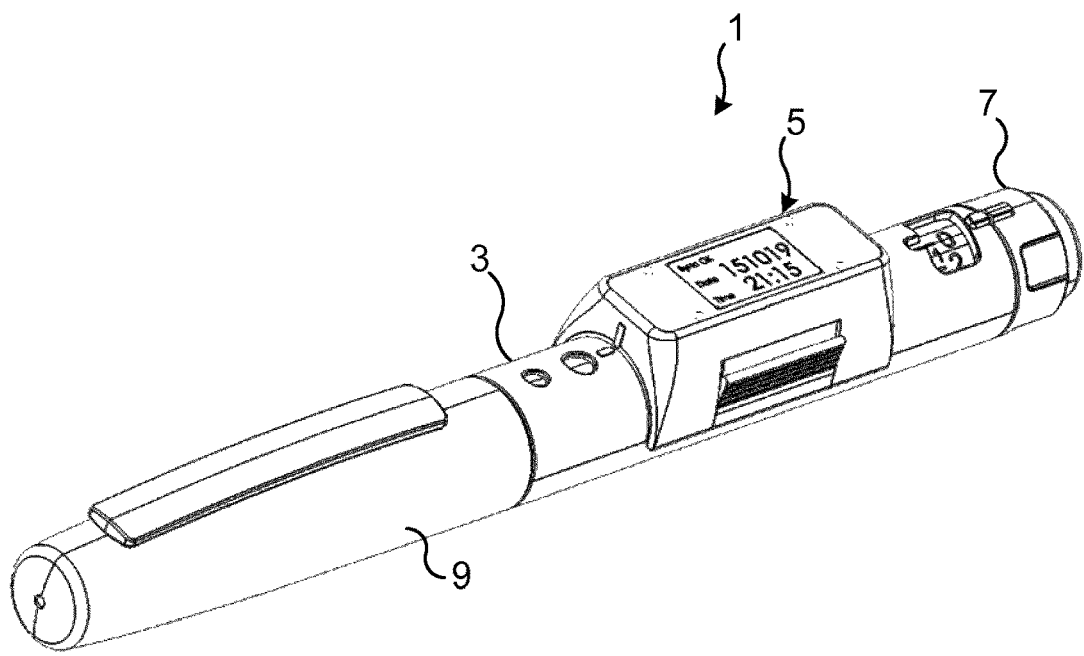
FIG. 1 schematically shows a perspective view of an example of a medicament delivery device.
Figure 2A:
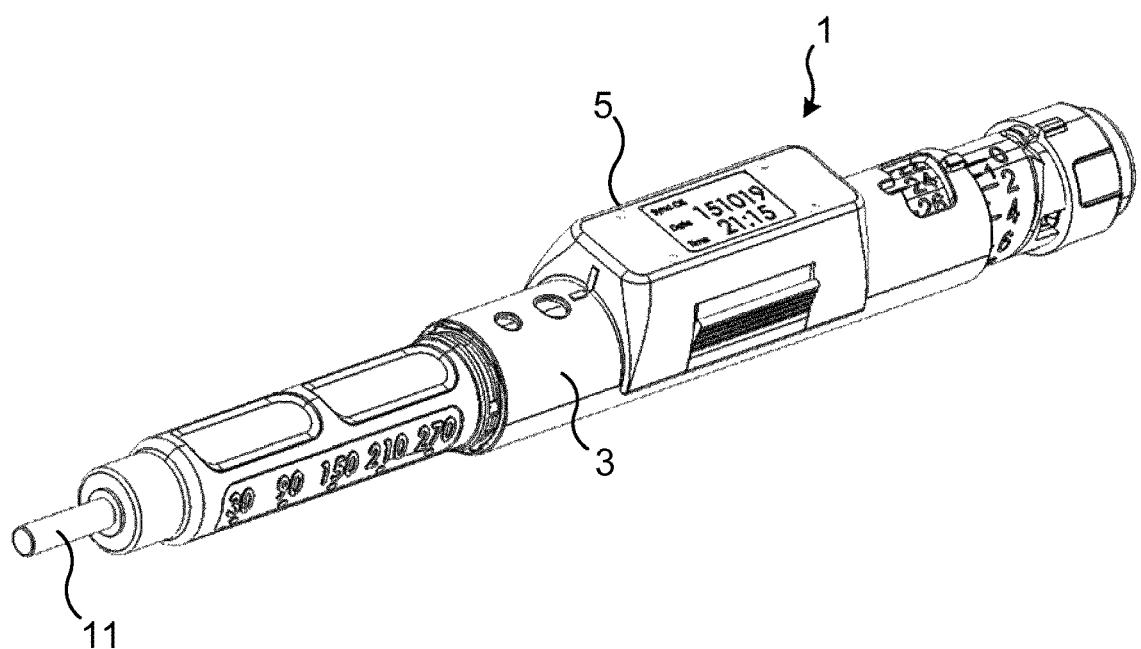
FIG. 2a shows a perspective view of the medicament delivery device in FIG. 1 without its proximal cover in a state in which a dose has been set.

With reference to FIG. 1 and FIGS. 2a and b, an example of a medicament delivery device 1 will now be described. In FIG. 1, the medicament delivery device 1 is in an initial state prior to a dose has been set.

Medicament delivery device 1 has a housing 3, a recording unit 5 and a dose setting member 7. The medicament delivery device 1 may also include a removable top cover 9.

The recording unit 5 is arranged to detect a medicament administration procedure by detecting rotation of the inner member of the medicament delivery device 1, and to generate dose expulsion data in response to detection of rotation of the inner member. The recording unit 5 may either be an add-on device detachable from the housing 3, or it may be integrated with the housing 3.

In FIG. 2a, the top cover 9 which covers a needle shield ii has been removed. Moreover, the medicament delivery device 1 is in a state in which a dose has been set by rotating the dose setting member 7. When the user grasps the dose setting member 7 and rotates it in a first direction, for example in clockwise direction, the dose setting member 7 and other components move distally, i.e. in the distal direction, as will be explained in detail below, in order to set a dose.

Figure 2B:
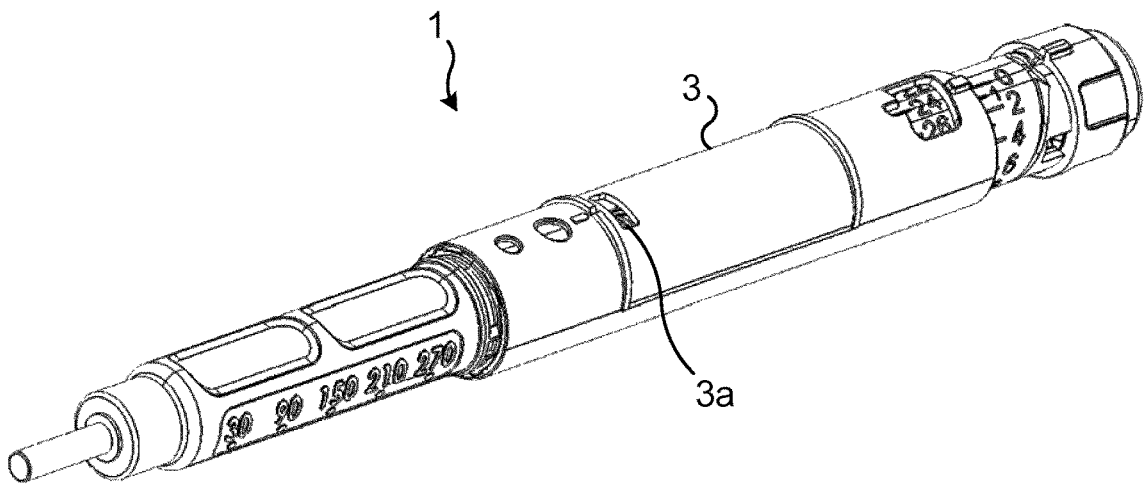
FIG. 2b shows the medicament delivery device in FIG. 2a without the recording unit.

FIG. 2b shows the medicament delivery device with the recording unit 5 detached from the housing 3. In variations in which the recording unit 5 is an add-on device, the housing 3 has an opening 3a, which forms part of a recording unit interface, exposing the interior of the medicament delivery device 1, in particular an inner member which will be described in more detail in what follows.

Figure 3:
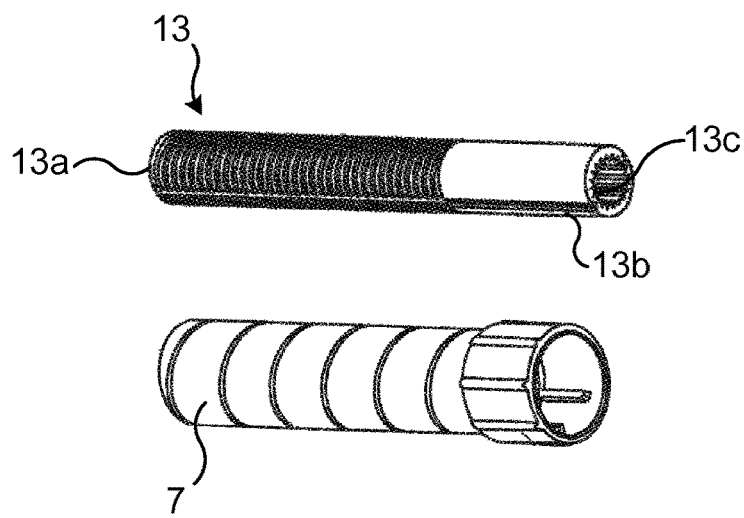
FIGS. 3-5 show examples of internal components of the medicament delivery device in FIG. 1.
Figure 4:
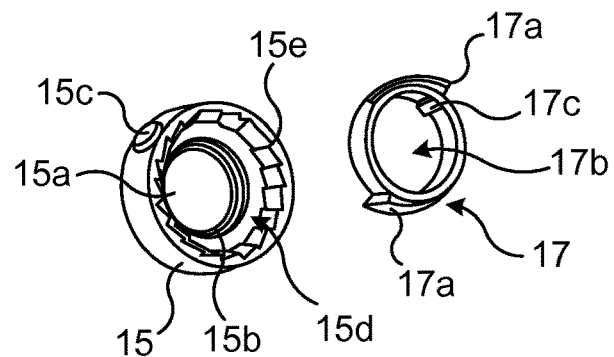
Figure 5:
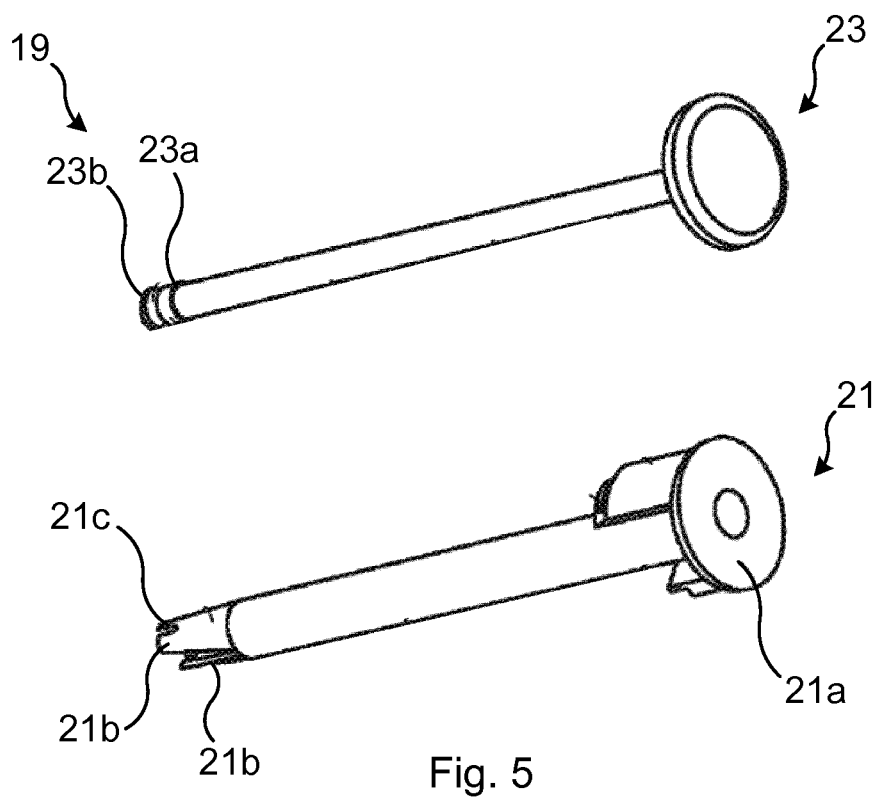

The general mechanical structure of an example of the medicament delivery device 1 is thoroughly described in WO2013058698 A1. Nevertheless, this structure will in essence be repeated herein. The detailed operation thereof will however not be repeated. Hereto, FIGS. 3-5 show additional exemplary components of the medicament delivery device 1. The medicament delivery device 1 has an elongated plunger rod 13 arranged inside the housing 3. The plunger rod 13 has a longitudinal axis generally corresponding with the longitudinal direction of the medicament delivery device 1. The plunger rod 13 is arranged with threads 13a on at least part of its outer surface. In the example shown in the FIG. 3, a proximal portion of the plunger rod 13 comprises a threaded structure. On its outer surface, the plunger rod 13 has at least one longitudinal groove 13b.

The medicament delivery device 1 furthermore includes an outer member 15, or thread insert, as shown in FIG. 4, arranged inside the housing 3. The plunger rod 13 is arranged to fit into the outer member 15 which is arranged with a central passage 15a, a through-hole. The centre of the central passage 15a generally coincides with the longitudinal axis of the medicament delivery device 1. The central passage 15a of the outer member 15 is arranged with threads 15b of complementary design to the threads 13a of the plunger rod 13. The outer surface of the outer member 15 may according to one example comprise a protrusion 15c or the like, fitting into a corresponding recess or through-hole on the inner surface of the housing 3, whereby the outer member 15 is locked to the housing 3. It may also be conceivable that the outer member and the housing are integrally.

The outer member 15 furthermore comprises a central bore 15d, which according to the example is located at the distal side of the outer member 15. The diameter of the central bore 15d is larger than the diameter of the central passage 15a so that a stepped configuration is provided. The inner circumferential surface of the central bore 15d is arranged with a circumferentially extending ratchet 15e arranged with saw-tooth shaped teeth.

The medicament delivery device 1 includes an annular inner member 17, a ring-shaped back rotating blocking element. The ratchet 15e cooperates with the inner member 17, which is arranged with two oppositely positioned flexible radial arms 17a, extending from the outer circumferential surface generally in the circumferential direction of the inner member 17. Although two such flexible radial arms 17a are shown in FIG. 4, a single flexible radial arm may as well suffice, or more than two arms may be provided, depending on the size of the inner member 17. The one or more flexible radial arms 17a are flexible in the generally radial direction. On the outwardly directed surfaces of the flexible radial arm(s) 17a, a ledge is arranged. Each ledge has a shape complementary to the ratchet 15e of the outer member 15. The inner member 17 is further arranged with a central passage 17b through which the plunger rod 13 extends. The central passage 17b is arranged with radially inwardly directed protrusions or ribs 17c, which protrusions 17c fit into the longitudinal grooves 13b on the outer surface of the plunger rod 13. This structure provides a rotational lock of the plunger rod 13 and the inner member 17. The plunger rod 13 and the inner member 17 are hence rotationally interlocked relative to each other.

The plunger rod 13 is further arranged with a plurality of longitudinal splines or ribs 13c provided on the inner circumferential surface of the hollow plunger rod 13.

The medicament delivery device 1 furthermore includes an activation button arrangement 19. The activation button arrangement 19 is linearly displaceable from a first position to a second position, in the proximal direction, to thereby provide first directional rotation of the plunger rod 13.

The activation button arrangement 19 includes a drive drum sleeve 21 of generally tubular shape arranged radially inside the plunger rod 13 and a resilient spinning member 23 received by the drive drum sleeve 21. The resilient spinning member 23 comprises a longitudinal rod and a distal push button.

The drive drum sleeve 21 is provided with a distal end wall 21a transversal to the longitudinal axis of the drive drum sleeve 21. The distal end wall 21a has a central opening and the drive drum sleeve 21 is hollow in order to receive the resilient spinning member 23 therein. The proximal end of the drive drum sleeve 21 comprises one or more, preferably two, flexible arms 21b extending in the proximal direction. The flexible arms 21b are flexible in that their proximal ends are radially deflectable upon application of a radial force thereon. The outer surface of each flexible arm 21b comprises a radially projecting plunger rod engagement protrusion 21c for selectively engaging with the longitudinal splines 13c on the inner surface of the plunger rod 13. The shape of the protrusions 21c generally corresponds to the shape of the circumferentially arranged splines 13c of the plunger rod 13.

The push button is intended to act as a contact surface for a finger of a user during drug delivery. As described above, the longitudinal rod of the resilient spinning member 23 is accommodated within the hollow drive drum sleeve 21. At its proximal end, the longitudinal rod comprises an engagement structure comprising a first circumferential ring-like protrusion 23a having a diameter larger than the diameter of the longitudinal rod and a second circumferential ring-like protrusion 23b having a diameter larger than the diameter of the longitudinal rod. The second protrusion 23b is preferably located at the proximal end of the longitudinal rod, and the first protrusion 23a is located distally from the second protrusion 23b.

The first protrusion 23a and the second protrusion 23b are axially spaced from each other such that a circumferential groove is formed therebetween. The size of the groove and the location on the longitudinal rod is such that the radially inwardly directed protrusion on the flexible arms 21b of the drive drum sleeve 21 is initially received in the groove. In such initial stage, the flexible arms 21b are not deflected radially outwards but are in a tension-free state.

The axial length of the resilient spinning member 23 in comparison to the drive drum sleeve 21 is such that in the initial state of the medicament delivery device, i.e. with the engagement protrusion being received in the groove, the proximal surface of the push button is spaced from the distal surface of the coupling element by a gap. This gap is maintained when a dose is set by a user. However, as soon as the push button is pushed in the proximal direction, the push button first bridges the gap thereby moving the longitudinal rod in proximal direction relative to the drive drum sleeve 21.

Due to such relative displacement, the distally located first ring-like protrusion 23a is pressed against the engagement protrusion on the flexible arms 21b, thus deflecting the flexible arms 21b radially outwardly and into engagement with the longitudinal splines 13c on the inner surface of the plunger rod 13.

Linear displacement of the resilient spinning member 23 results in rotation, in the first direction, of the drive drum sleeve 21 due to interaction with the rotating dose setting member 7. Since the protrusions 23a engage with the longitudinal splines 13c, the plunger rod 13 also starts to rotate in the first direction and is thereby displaced linearly in the proximal direction as its threads 13a interact with the threads 15b of the outer member 15.

Figure 6:
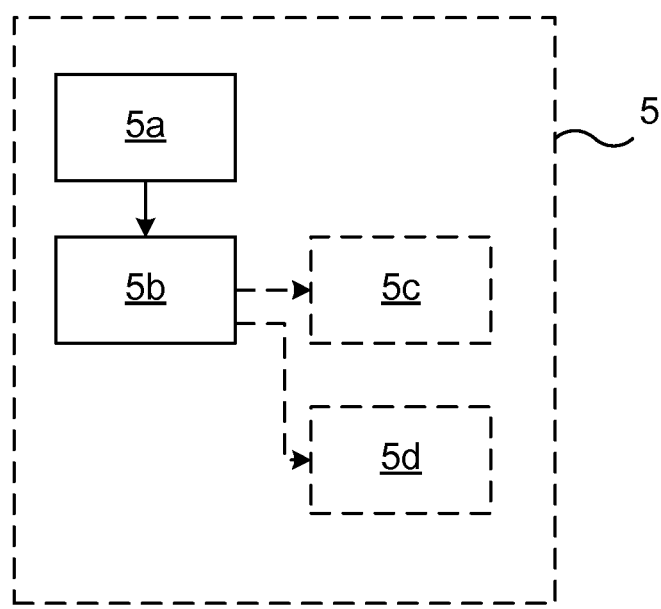
FIG. 6 shows a block diagram of an example of a recording unit.

FIG. 6 illustrates electronic components of the medicament delivery device 1. In particular, the recording unit 5 comprises a first sensor 5a configured to detect rotation of the inner member 17, and processing circuitry 5b configured to generate dose expulsion data in response to detection of rotation of the inner member 17 and thus of rotation of the plunger rod 13.

The processing circuitry 5b uses any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations.

The dose expulsion data may for example comprise information about the date and time when the last dose of medicament was administered. It may also comprise information of whether synchronisation for data transfer to an external device has been successful or not. The dose expulsion data may according to one variation also include information about the size of the latest dose taken.

The recording unit 5 may according to one variation comprise a transmitter 5c arranged to wirelessly transmit the dose expulsion data generated by the processing circuitry 5b, to an external device such as a smart device, e.g. a smart phone or a tablet computer, or to a personal computer. The transmitter 5c hence includes an antenna, which may be arranged to transmit the dose expulsion data over for example Bluetooth®, Wi-Fi™ or a cellular radio access network (RAN) such as Wideband Code Division Multiple Access (WCDMA) Long Term Evolution (LTE) and the 5G standard.

According to one variation, a unique identifier of the recording unit 5 may be transmitted with the dose expulsion data when a dose of medicament has been administered. This may facilitate compliance/adherence.

The recording unit 5 may also comprise a display unit 5d arranged to display the dose expulsion data. The display unit 5d has a display, for example an electrophoretic (E-ink) display.

The recording unit 5 may furthermore comprise an energy storage unit. The energy storage unit may be configured to power the first sensor 5a, and any other electronic component such as the processing circuitry 5b, and the transmitter 5c, if present. The energy storage unit may for example be a battery.

Figure 7:
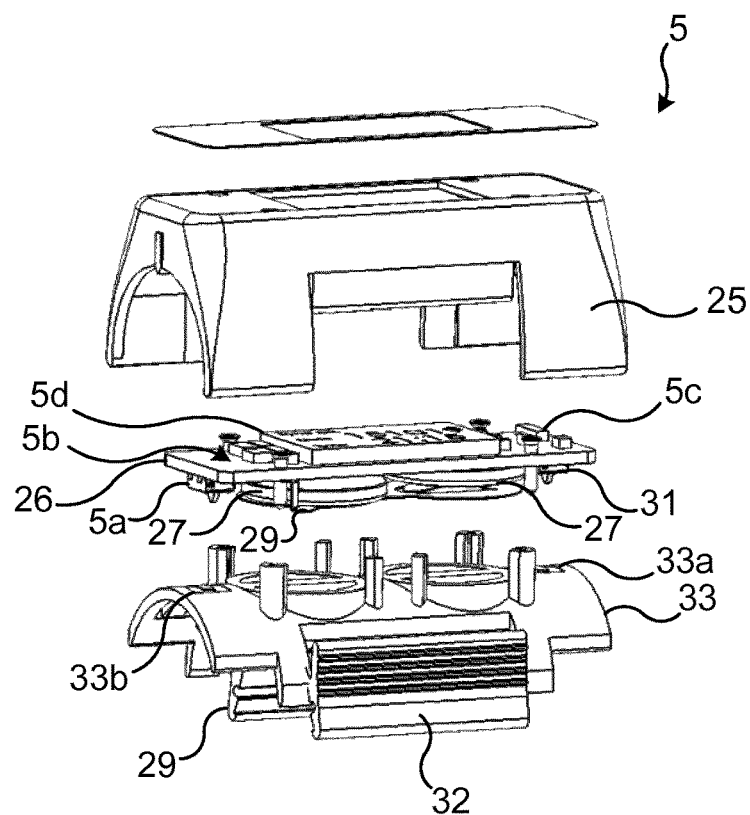
FIG. 7 shows an exploded view of an example of a recording unit.

FIG. 7 shows one example of a recording unit 5. According to this example, the recording unit 5 is of the detachable type, i.e. it can be attached to and detached from the housing 3 of the medicament delivery device 1. The recording unit 5 has a recording unit housing 25, and a circuit board 26 provided with the display unit 5d, the first sensor 5a, the processing circuitry 5b and the transmitter 5c. The recording unit 5 furthermore comprises batteries 27, battery connectors 29, a second sensor 31, a circuit board support 33, and two lock members 32 arranged to lock the recording unit 5 to the housing 3 of the medicament delivery device 1.

The lock members 32 are pivotally mounted to the recording unit housing 25. The lock members 32 may thus be lock hinges arranged to pivot along a respective axis parallel with respect to the longitudinal axis of the recording unit 5. The lock members 32 may thereby be pivoted between a respective open position in which the recording unit 5 can be mounted to the housing 3 and a respective closed position in which the lock members 32 lock the recording unit 5 to the housing 3. The recording unit 25 may have flexible walls arranged to push the locking members 29 to pivot towards their locking position.

The second sensor 31 is arranged to detect whether the recording unit 5 is mounted to the housing 3 or not. It can thereby be detected whether the recording unit 5 is mechanically connected to the housing 3. The second sensor 31 is arranged to activate the electronic components of the recording unit 5, e.g. the first sensor 5a, the processing circuitry 5b, and the transmitter 5c, if present.

The second sensor 31 may for example be an electromechanical switch which is arranged to be actuated when the recording unit 5 is mounted to the housing 3. The circuit board support 33 has a through-hole 33a through which the second sensor 31 extends below the circuit board support 33. The second sensor 31 may thereby be actuated upon contact with the housing 3.

The circuit board support 33 may according to one variation have a through-hole 33b arranged to receive the first sensor 5a, such that the first sensor 5a extends through and beyond the circuit board support 33, into the housing 3 via the opening 3a.

A number of examples of the medicament delivery device 1 will now be described with reference to FIGS. 8-13b. In these figures, the inner member 17, and the first sensor 5a are shown in a number of variations together with the circuit board 26 to which the first sensor 5a is mounted. Most other parts have been removed for reasons of clarity.

Figure 8:
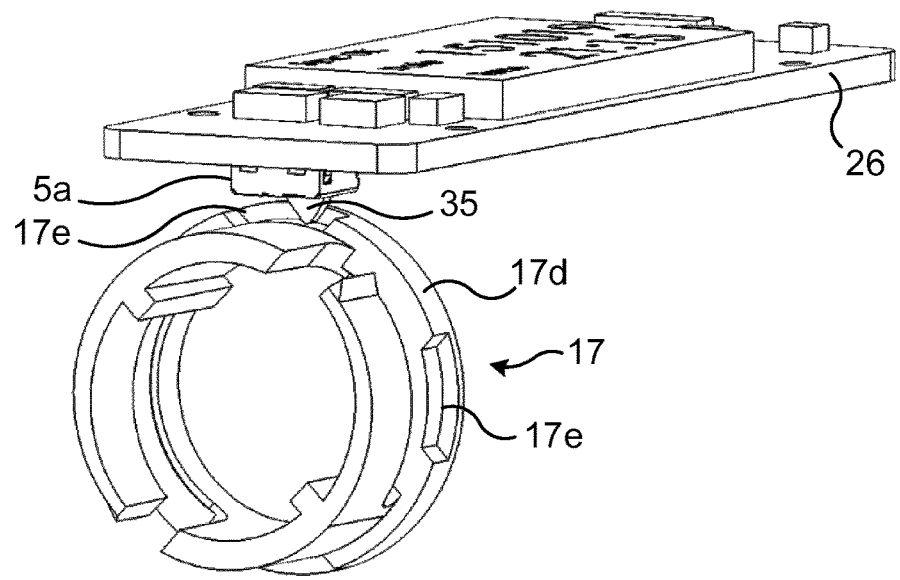
FIG. 8 shows a perspective view of a first example of the first sensor and the inner member.

FIG. 8 shows a first example, where the inner member 17 has an outer periphery 17d provided with a plurality of recesses 17e. The first sensor 5a is in this example an electromechanical switch, having a movable member 35 arranged to be received in the recesses 17e. Thus, as the inner member 17 rotates concurrently with the plunger rod 13, the movable member 35 is moved in and out of the recesses 17e. Rotation of the inner member 17 can thereby be detected. The processing circuitry 5b will thus generate dose expulsion data based on the detected rotation of the inner member 17.

The number of recesses 17b influences the possibility to detect small rotations of the inner member 17 as well as for some variations the resolution forming basis for determining the amount of medicament that has been administered by means of the recording unit 5. The inner member 17 and in particular the recesses 17e should thus preferably be designed with dose size and corresponding rotation of the inner member 17 in mind.

The processing circuitry 5b is according to one variation configured to determine the number of times the electromechanical switch is moved in and out from the recesses 17e during one drug administration. Moreover, the processing circuitry 5b may be configured to determine an injected dose based on the determined number of times the electromechanical switch is moved in and out from the recesses 17e.

Figure 9:
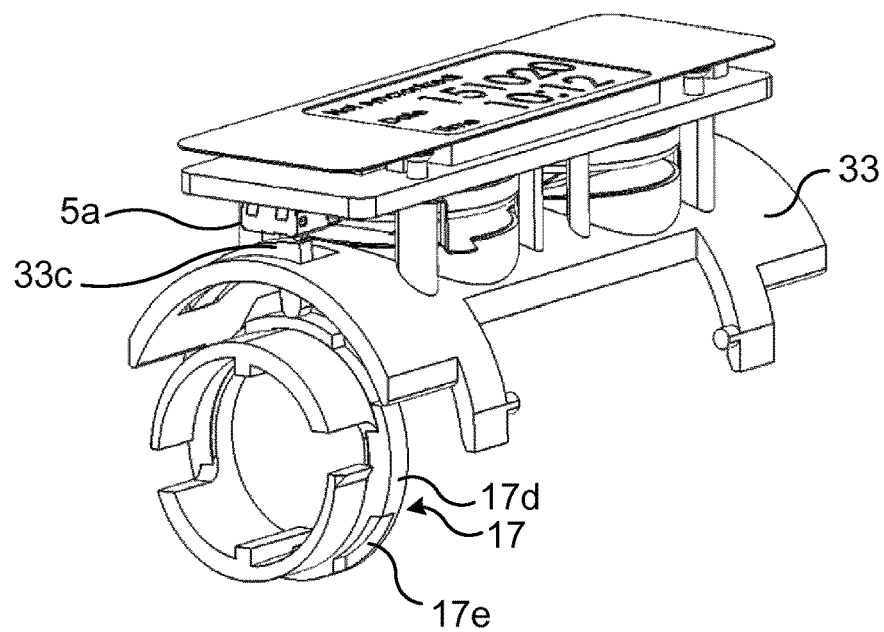
FIG. 9 shows a perspective view of a variation of the first sensor and the inner member shown in FIG. 8.

FIG. 9 shows a variation of the first example shown in FIG. 8. Here, the first sensor 5a is also an electromechanical switch, and the outer periphery 17d of the inner member 17 is provided with the recesses 17e. A difference is that the circuit board support 33 has a flexible arm 33c radially inwards of and radially aligned with the first sensor 5a. The flexible arm 33c has an end portion arranged to be received by the recesses 17e. As the flexible arm 33c moves in and out of the recesses 17e, the flexible arm 33c actuates the movable member of the first sensor 5a. In this manner, rotation of the inner member 17 and thus of the plunger rod 13 may be detected.

Figure 10:
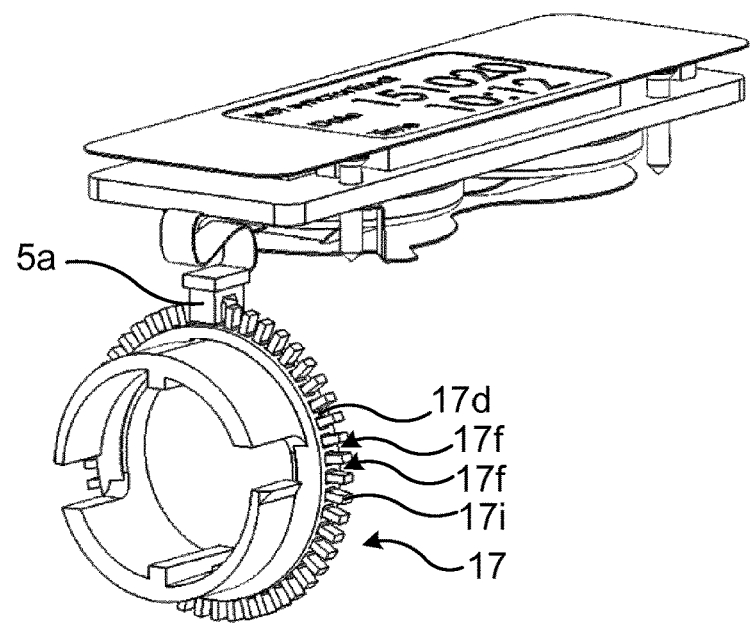
FIG. 10 shows a perspective view of a second example of the first sensor and the inner member.

FIG. 10 shows another example, in which the first sensor 5a is a photo interrupter having an electromagnetic wave emitter and an electromagnetic wave sensor. The outer periphery 17d of the inner member 17 is provided with a plurality of through-openings 17f. The through-openings 17f are according to the example shown in FIG. 10 formed between radial protrusions 17i, but could alternatively for example be through-holes. The through-openings 17f are arranged to extend in between the electromagnetic wave emitter and the electromagnetic wave sensor. To this end, the electromagnetic wave sensor can detect electromagnetic waves emitted by the electromagnetic wave emitter, propagating between the cogs 17f. As a result, rotation of the inner member 17 can be detected and the processing circuitry 5a can thereby generate dose expulsion data.

According to one variation, the dose may also be determined, based on the number of times an electromagnetic wave is detected by the electromagnetic wave sensor.

Figure 11:
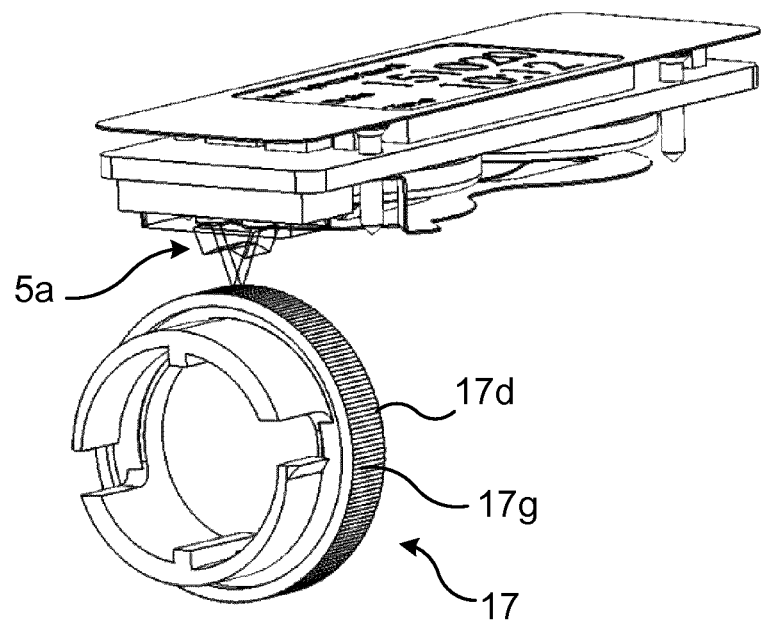
FIG. 11 shows a perspective view of a third example of the first sensor and the inner member.

FIG. 11 shows yet another example, in which the first sensor 5a comprises an optical sensor, and the recording unit 5 comprises an image acquisition unit and an electromagnetic wave emitter. Furthermore, the outer periphery 17d of the inner member 17 is provided with a visual pattern 17g. The visual pattern 17g may for example contain a plurality of axial stripes distributed along the outer periphery 17d. According to one variation each stripe corresponds to one dose unit.

The electromagnetic wave emitter is configured to emit electromagnetic waves onto the visual pattern and the first sensor 5a is arranged to capture electromagnetic waves reflected by the visual pattern.

The image acquisition unit is configured to generate images of captured reflected electromagnetic waves and the processing circuitry 5b is configured to determine whether the inner member 17 is being rotated, based on the images. Hence, an image analysis is performed by the processing circuitry 5b in order to determine whether the inner member 17 is being rotated.

Figure 12A:
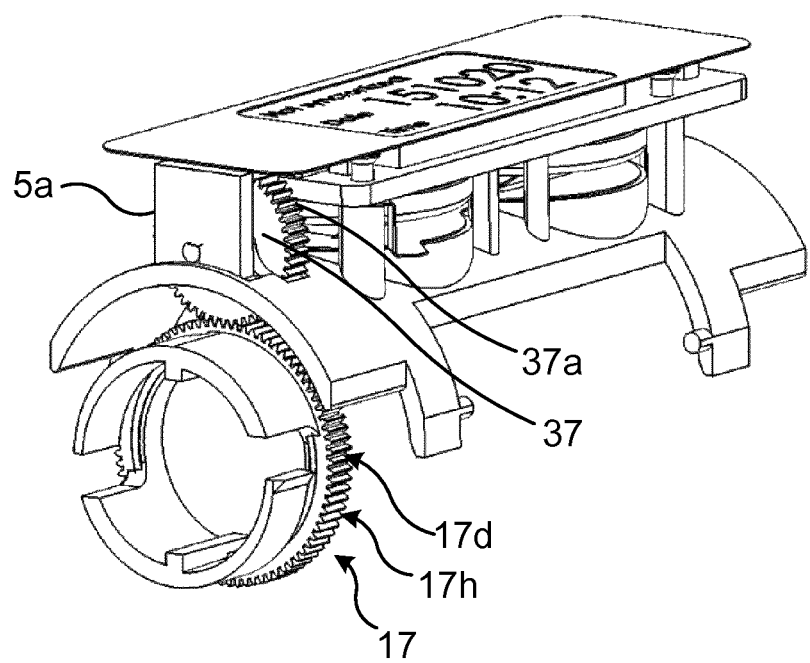
FIG. 12a shows a perspective view of a fourth example of the first sensor and the inner member.

In the example in FIG. 12a, the inner member 17 has an outer periphery 17d provided with a plurality of first cogs 17h and the recording unit 5 includes a cog wheel 37 provided with a plurality of second cogs 37a arranged to engage with the first cogs 5e. The first sensor 5a is configured to detect rotation of the inner member 17 by detecting rotation of the cog wheel 37.

The first sensor 5a may for example be a photo interrupter having an electromagnetic wave emitter and an electromagnetic wave sensor. The second cogs 37 may in this case be are arranged to extend in between the electromagnetic wave emitter and electromagnetic wave sensor.

According to another example, the first sensor 5a may be a rotary position sensor arranged to detect rotation of the inner member 17 by detecting rotation of the cog wheel 37.

Figure 12B:
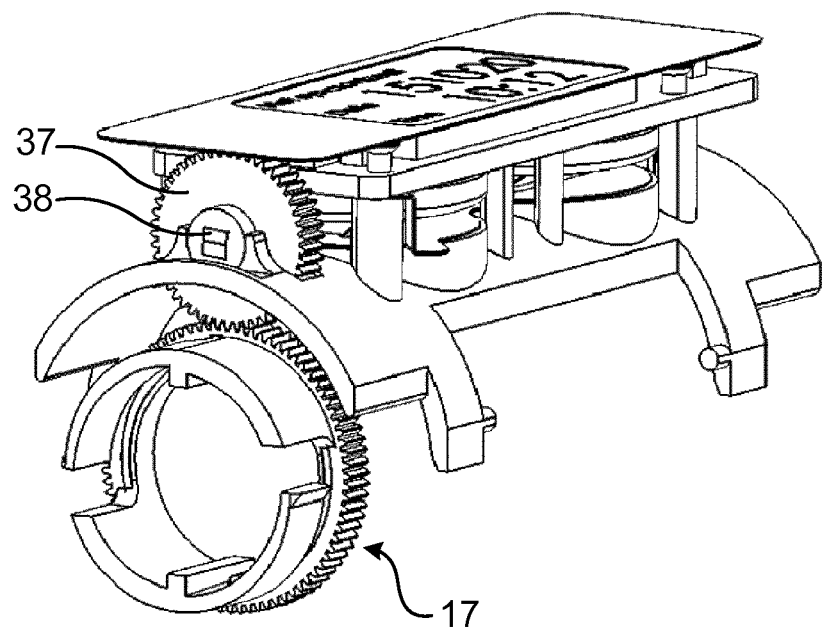

According to yet another example, the cog wheel 37 may include a magnet 38 as shown in FIG. 12b, wherein the first sensor 5a, in the same position as in FIG. 12a but not shown in FIG. 12b to expose the magnet 38, is a contactless magnetic sensor such as a magnetic rotary encoder, magnetic position sensor or a Hall sensor, arranged to detect rotation of the inner member 17 by detecting rotation of the cog wheel 37.

Figure 13A:
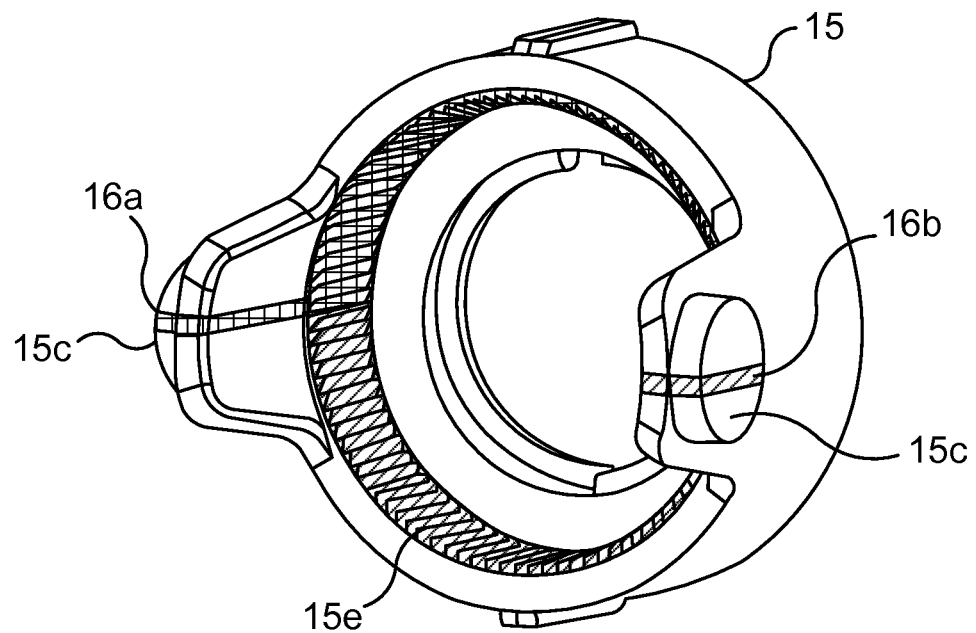
FIGS. 13a and 13b show perspective view of examples of the outer member.

FIG. 13a shows yet another example of the medicament delivery device 1. In FIG. 13a only an example of the outer member 15 is shown. The outer member 15 has a first electric terminal 16a and a second electric terminal 16b. The first electric terminal 16a may be provided on one of the protrusions 15c and the second electric terminal 16b may be provided on another one of the protrusions 15c, both being arranged to be received in a recess or through-hole of the housing 3. The teeth of the ratchet 15e are electrically conductive.

The teeth may for example have been made conductive by applying a conductive coating, or by means of Laser Direct Structuring (LDS).

A first set of teeth are electrically connected to the first electric terminal 16a, as illustrated by the essentially vertical lines and a second set of teeth are electrically connected to the second electric terminal 16b as illustrated by the diagonal lines. According to the example in FIG. 13a, the first set of teeth form a continuous half circle along the inner periphery of the outer member 15 and the second set of teeth form the other half circle of the inner periphery.

The flexible radial arms 17a of the inner member 17 are electrically conductive and in electrical connection with each other. This electrical conductivity can for example be made by applying a conductive coating or by means of LDS.

According to this example, the recording unit 5 furthermore has a power supply connectable to the first electric terminal 16a and to the second electric terminal 16b. The power supply may for example be the batteries 27.

The first sensor 5a is configured to detect rotation of the inner member 17 by detecting whenever there is a closed circuit between the first electric terminal 16a and the second electric terminal 16b, i.e. when current is able to flow from e.g. the first electric terminal 16a to the second electric terminal 16b via the inner member 17.

Figure 13B:
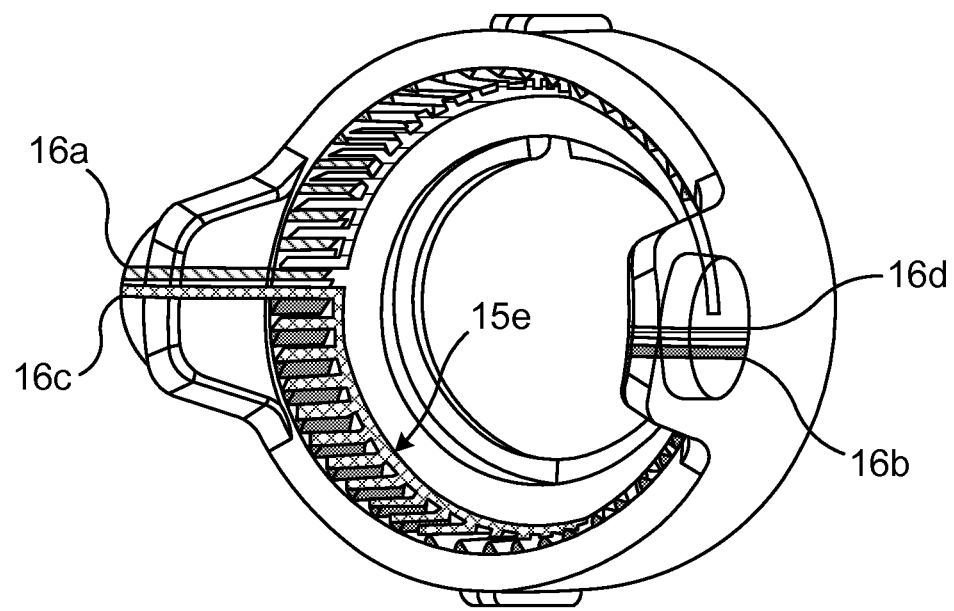

FIG. 13b shows a variation of the arrangement in FIG. 13a. Here, the outer member 15 has two additional electric terminals so that there are four electric terminals in total, the first electric terminal 16a, the second electric terminal 10, a third electric terminal 16c and a fourth electric terminal 16d. The teeth of the ratchet 15e are conductive and are connected in an alternating manner; in a first half circle of the inner periphery of the outer member 15 every other tooth is connected to the first electric terminal 16a, corresponding to the first set of teeth, and every other tooth is connected to the fourth electric terminal 16d, corresponding to a fourth set of teeth. In a second half circle every other tooth is connected to the second electric terminal 16b, corresponding to the second set of teeth, and every other tooth is connected to the third electric terminal 16c, corresponding to a third set of teeth. This design is beneficial in that it may provide more accurate detection than in the case where only two electric terminals are used, especially because it enables better handling of contact bounces.

In the example in FIG. 13b, the protrusions 15c may be provided with the electric terminals; there may for example be two terminals per protrusion 15c. The first electric terminal 16a and the third electric terminal 16c may for example be provided on one protrusion and the second electric terminal 16b and fourth electric terminal 16d may be provided on another protrusion 15c.

Figure 13C:
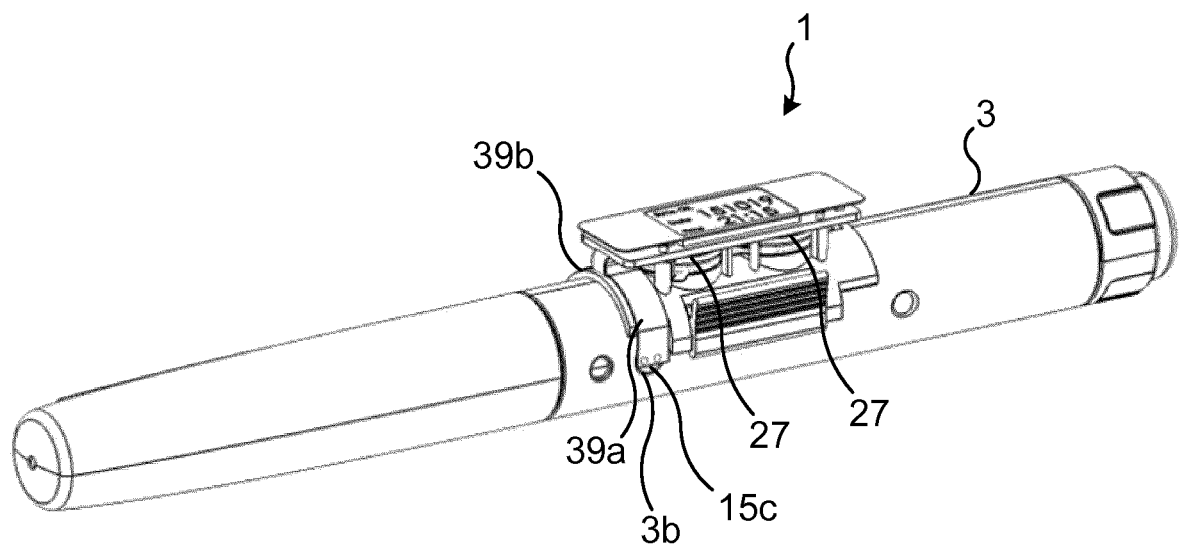
FIG. 13c shows a perspective view of a medicament delivery device including one of the outer members depicted in FIGS. 13a and b.

FIG. 13c shows an example of a medicament delivery device 1 that includes an outer member 15 of the type shown in FIG. 13a or FIG. 13b. Here, the recording unit housing has been removed to expose the power supply, exemplified by batteries 27, and electrode arrangements 39a and 39b connected to the power supply and to the electric terminals of the outer member 15. The protrusions 15c of the outer member 15 extend through a respective through-hole 3b of the housing 3, of which through-holes only one is visible in FIG. 13c. Each electrode arrangement 39a, 39b may have one or two electrodes, depending on the whether the outer member 15 has two electric terminals, one on each protrusion 15c, as in the example in FIG. 13a or four electrodes, two on each protrusion 15c, as in the example shown in FIG. 13b.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device comprising:
   a housing having a through-hole located in a distal portion of the housing,
   a plunger rod received by the housing, which plunger rod is rotatable in a first direction relative to the housing and linearly displaceable thereby,
   an activation button arrangement linearly displaceable from a first position to a second position to thereby rotate the plunger rod in the first direction,
   a second direction rotation preventer having an annular outer member that is rotationally fixed relative to the housing and an annular inner member partially received by the outer member,
   wherein the outer member and the inner member are arranged to receive the plunger rod and wherein the inner member is rotationally interlocked with the plunger rod,
   wherein the outer member and the inner member are structured to allow the inner member to rotate in the first direction relative to the outer member and to prevent the inner member from rotating in a second direction opposite to the first direction, and
   a recording unit mounted on an outside surface of the housing and aligned with the through-hole, where the recording unit comprises:
   a first sensor comprising a part that radially extends through the through-hole where the part is adjacent to the inner member and is configured to detect rotation of the inner member, and
   processing circuitry configured to generate dose expulsion data in response to detection of rotation of the inner member.

2. The medicament delivery device as claimed in claim 1, wherein one of the inner member and the outer member has a ratchet along the circumference thereof and the other one of the inner member and the outer member has a flexible radial arm arranged to interact with the ratchet, to allow rotation of the inner member in the first direction and to prevent rotation of the inner member in the second direction.

3. The medicament delivery device as claimed in claim 1, wherein the recording unit is integrated with the housing.

4. The medicament delivery device as claimed in claim 1, comprising a display unit configured to display the dose expulsion data.

* * * * *